US009060987B2

(12) United States Patent
Lavan et al.

(10) Patent No.: US 9,060,987 B2
(45) Date of Patent: *Jun. 23, 2015

(54) METHODS FOR TREATING GOUT FLARES

(71) Applicant: CymaBay Therapeutics, Inc., Newark, CA (US)

(72) Inventors: Brian Edward Lavan, San Francisco, CA (US); Gopal Chandra Saha, Dublin, CA (US); Charles A. McWherter, Oakland, CA (US); Brian K. Roberts, Palo Alto, CA (US)

(73) Assignee: CYMABAY THERAPEUTICS, INC., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/668,003

(22) Filed: Nov. 2, 2012

(65) Prior Publication Data

US 2014/0128438 A1 May 8, 2014

Related U.S. Application Data

(60) Provisional application No. 61/556,052, filed on Nov. 4, 2011.

(51) Int. Cl.
| | | |
|---|---|---|
| *A61K 31/192* | (2006.01) | |
| *A61K 31/216* | (2006.01) | |
| *A61K 31/426* | (2006.01) | |
| *C07C 59/68* | (2006.01) | |
| *C07C 233/47* | (2006.01) | |

(52) U.S. Cl.
CPC ............. *A61K 31/216* (2013.01); *A61K 31/192* (2013.01); *A61K 31/426* (2013.01); *C07C 59/68* (2013.01); *C07C 233/47* (2013.01)

(58) Field of Classification Search
CPC .. A61K 31/192; A61K 31/216; A61K 31/426
See application file for complete search history.

(56) References Cited

U.S. PATENT DOCUMENTS

| | | | |
|---|---|---|---|
| 3,517,050 | A | 6/1970 | Bolhofer et al. |
| 4,250,191 | A | 2/1981 | Edwards |
| 5,021,448 | A | 6/1991 | Piraino et al. |
| 5,057,427 | A | 10/1991 | Wald et al. |
| 5,077,217 | A | 12/1991 | Matson et al. |
| 6,262,118 | B1 | 7/2001 | Luskey et al. |
| 6,613,802 | B1 | 9/2003 | Luskey et al. |
| 6,624,194 | B1 | 9/2003 | Luskey et al. |
| 6,646,004 | B1 | 11/2003 | Luskey et al. |
| 7,199,259 | B2 | 4/2007 | Daugs et al. |
| 7,432,394 | B2 | 10/2008 | Cheng et al. |
| 7,576,131 | B2 | 8/2009 | Luskey et al. |
| 7,714,131 | B2 | 5/2010 | Zhu et al. |
| 2003/0220399 | A1 | 11/2003 | Luskey et al. |
| 2010/0093854 | A1 | 4/2010 | Broggini et al. |
| 2010/0160351 | A1 | 6/2010 | Jenkins et al. |
| 2011/0268801 | A1 | 11/2011 | Quart et al. |

FOREIGN PATENT DOCUMENTS

| | | |
|---|---|---|
| WO | 2009/151695 | 12/2009 |
| WO | 2011/032175 | 3/2011 |
| WO | WO2011032175 | 3/2011 |

OTHER PUBLICATIONS

Brook R.A. et al. "Chronic gout: epidemiology, disease progression, treatment and disease burden". Current Medical Research & Opinion, vol. 26, No. 12, 2010, pp. 2813-2821.*
Becker et al., New Englan Journal of Medicine, v. 353, No. 23, pp. 2450-2461 (Dec. 8, 2005).
Edwards, Cleveland Clinic Journal of Medicine, v. 75, pp. S14-S16 (2008).
El-Zawawy et al., Cleveland Clinic Journal of Medicine, v. 77, pp. 919-927 (2010).
Hutchison et al., Atherosclerosis, v. 18, No. 3, pp. 353-362 (Nov. 1973).
Keller et al., Arzneimittel-Forschung/Drug Research, v. 26, No. 16, pp. 2221-2224 (1976)—Abstract Only.
Aronow et al., Current Therapeutic Research, v. 15, pp. 902-906 (1973).
Stockert et al., Clinical Medicine Insights: Therapeutics, v. 2, pp. 927-945 (2010).
Whitehouse et al., Annals of the New York Academy of Sciences, v. 226, pp. 309-318 (1973).
Li et al., Relationship Between Physical Properties and Crystal Structures of Chiral Drugs, Pharm. Sci. 86:1073-77 (1997).
Rautio et al., Prodrugs: design and clinical applications, Nat. Rev. Drug Discov., 7, 255-270 (2008).
Higuchi et al., Pro-drugs as Novel Delivery Systems, vol. 14, A.C.S. Symposium Series (1975).
Lochmuller, Chromatography, 113, 283-302 (1975).
Tirosh et al., Normal fasting plasma glucose levels and type 2 diabetes in young men, N. Engl. J. Med., 353:1454-62 (2005).
Torres et al., Hyperalgesia, synovitis and multiple biomarkers of inflammation are suppressed by interleukin 1 inhibition in a novel . . ., Ann. Rheum. Dis. 68:1602-08 (2009).
Liu-Bryan et al., Innate Immunity Conferred by Toll-like Receptors 2 and 4 and Myeloid Differentiation Factor 88 Expression Is Pivotal . . ., Arthritis Rheum. 52:2936-46 (2005).
Bluhm et al., Abstract: "A double blind study comparing halofenate with probenecid in gout", Arthritis Rheum., 18(4), 388-389 (1975).
Anonymous, Press release: "Metabolex Initiates Phase 2 Trial of Arhalofenate Potential Best-in-Class Uricosuric Agent for the Treatment of Gout", Internet citation, May 19, 2011. Currently retrievable at http://ir.cymabay.com/press-releases/detail/74/metabolex-initiates-phase-2-trial-of-arhalofenate.
Schlesinger, PubMed abstract of: "Management of acute and chronic gouty arthritis: present state-of-the-art", Drugs, 64(21), 2399-2416 (2004). Retrievable at http://www.ncbi.nlm.nih.gov/pubmed/15481999.

(Continued)

*Primary Examiner* — Renee Claytor
(74) *Attorney, Agent, or Firm* — Sam L. Nguyen; Hamilton, DeSanctis & Cha, LLP

(57) ABSTRACT

Methods of treating gout flares comprising administering a composition comprising a first urate-lowering agent are disclosed. In some aspects, the first urate-lowering agent is (−)-halofenate, (−)-halofenic acid, or a pharmaceutically acceptable salt thereof. Other aspects provide for methods of reducing the number, duration, frequency or intensity of gout flares experienced by a subject.

16 Claims, 7 Drawing Sheets

(56) References Cited

OTHER PUBLICATIONS

Anturane Full Prescribing Information, downloaded from http://www.drugs.com/pro/anturane.html.
Benzbromarone Prescriber Information, downloaded from http://www.rheumatology.org.nz.
Krystexxa Full Prescribing Information, downloaded from http://www.krystexxa.com/.
Probenecid Full Prescribing Information, downloaded from http://dailymed.nlm.nih.gov/dailymed/getFile.cfm?setid=ae126418-5474-4fbe-b83c-bde8b2b4ae6e&type=pdf&name=ae126418-5474-4fbe-b83c-bde8b2b4ae6e.
Uloric Full Prescribing Information, downloaded from http://www.uloric.com.
Zyloprim Product Information, downloaded from www.prometheuslabs.com/Resources/PI/Zyloprim.pdf.
Mitha et al., "Rilonacept for gout flare prevention during initiation of uric acid-lowering therapy: results from the Presurge-2 international, phase 3, randomized, placebo-controlled trial", Rheumatology, v. 52(7), pp. 1285-1292 (2013).
Schlesinger, "Treatment of Chronic Gouty Arthritis: It Is Not Just About Urate-Lowering Therapy", Semin. Arthritis Rheum., v. 42. pp. 155-165 (2012).
Sundy et al., "Rilonacept for Gout Flare Prevention in Patients Receiving Uric Acid-lowering Therapy: Results of Resurge, a Phase III, International Safety Study", J. Rheumatol., v. 41(8), pp. 1703-1711 (2014).
CymaBay Therapeutics, Inc., "CymaBay Therapeutics announces positive results from its Phase 2b clinical study demonstrating that arhalofenate met the primary endpoint of reduction in gout flares", press release, Feb. 24, 2015, downloaded from http://ir.cymabay.com/press-releases/detail/264/cymabay-therapeutics-announces-positive-results-from-its-phase-2b-clinical-study-demonstrating-that-arhalofenate-met-the-primary-endpoint-of-reduction-in-gout-flares.
Aronow et al., "Effect of halofenate on serum uric acid", Clin. Pharmacol. Ther., 14(3), 371-373 (1973).
Aronow et al., "Long-term effect of halofenate on serum lipids", Curr. Ther. Res., 16(9), 897-903 (1974).
Aronow et al., "Long-term efficacy of halofenate on serum triglyceride levels", Curr. Ther. Res., 18(5), 855-861 (1975).
Baer, "Monitoring of plasma levels of a hypolipemic agent", Clin. Pharmacol. Ther., 16(1, Part 2), 272-273 (1974).
Bassett et al., "Effects of halofenate and probenecid on serum lipids and uric acid in hyperlipidemic, hyperuricemic adults", Clin. Pharmacol. Ther., 22(3), 340-351 (1977).
Bluestone et al., "Halofenate Its selection and trial as a primary uricosuric agent", Arthritis Rheumatism, 18(6), 859-862 (1975).
Dujovne et al., "One-year trials with halofenate, clofibrate, and placebo", Clin. Pharmacol. Ther., 19(3), 352-359 (1976).
Dujovne et al., "A two-year crossover therapeutic trial with halofenate and clofibrate", Am. J. Med. Sci., 272(3), 277-284 (1976).
Fanelli et al., "Renal excretion and uricosuric properties of halofenate, a hypolipidemic-uricosuric agent, in the chimpanzee", J. Pharmacol. Exp. Ther., 180(2), 377-396 (1972).
Jain et al., "The effect of MK-185 on some aspects of uric acid metabolism", Clin. Pharmacol. Exp. Ther., 11(4), 551-557 (1970).
Krut et al., "Comparison of Clofibrate with Halofenate in Diabetics with Hyperlipidaemia", S. Afr. Med. J., 51, 348-352 (1977).
Kudzma et al., "Potentiation of Hypoglycemic Effect of Chlorpropamide and Phenformin by Halofenate", Diabetes, 26 (4), 291-295 (1977).
Morgan et al., "Hypolipidemic, uricosuric, and thyroxine-displacing effects of MK-185 (halofenate)", Clin. Pharmacol. Ther., 12(3), 517-524 (1971).
Rottiers et al., "A one year double bind study of the effect of halofenate and clofibrate in patients with hyperlipoproteinemia", Acta Clinica Belgica, 30(5), 398-408 (1975).

\* cited by examiner

METHODS FOR TREATING GOUT FLARES

CROSS-REFERENCE TO RELATED APPLICATIONS

This application claims priority to U.S. Provisional Application No. 61/556,052 filed on Nov. 4, 2011, the complete disclosure of which is incorporated by reference herein.

BACKGROUND

This application relates to the treatment, including the prevention, of gout flares.

SUMMARY

This application describes methods of treating a gout flare experienced by a subject comprising administering to the subject a compound of Formula (I)

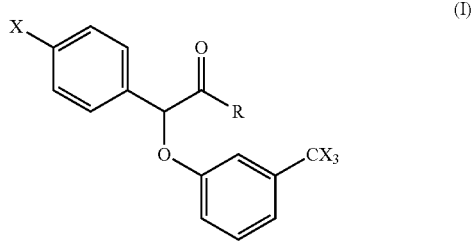

(I)

wherein R is selected from the group consisting of a hydroxy, lower aralkoxy, di-lower alkylamino-lower alkoxy, lower alkanamido-lower alkoxy, benzamido-lower alkoxy, ureido-lower alkoxy, N'-lower alkyl-ureido-lower alkoxy, carbamoyl-lower alkoxy, halophenoxy substituted lower alkoxy, carbamoyl substituted phenoxy, carbonyl-lower alkylamino, N,N-di-lower alkylamino-lower alkylamino, halo substituted lower alkylamino, hydroxy substituted lower alkylamino, lower alkanolyloxy substituted lower alkylamino, ureido, and lower alkoxycarbonylamino; and each X is independently a halogen, or a pharmaceutically acceptable salt thereof.

Other aspects provide for methods of reducing the number, duration, frequency or intensity of gout flares experienced by a subject comprising administering a compound of Formula (I) or a pharmaceutically acceptable salt thereof to the subject. Other aspects provide for the treatment of hyperuricemia in a subject with gout comprising administering to a subject in need thereof a compound of Formula (I), wherein the dose, frequency, and duration of administration are effective to reduce the number, duration, frequency, or intensity of gout flares experienced by the subject during the duration. Yet other aspects provide for methods of providing to a subject (−)-halofenic acid with an intraday peak-to-trough ratio of about 2.0 or less. Further aspects are provided below.

Uric acid lowering agents such as allopurinol and febuxostat generally increase the number, duration, frequency, or intensity of gout flares upon initiation of therapy, and this exacerbation may last for several weeks to months following initiation of such therapy. Uric acid lowering agents often require a dose titration strategy in which the dose is progressively increased to the therapeutic dose in order to minimize the number, duration, frequency, or intensity of flares. Flare treatment or prophylaxis with an additional therapeutic agent such as a non-steroidal anti-inflammatory agent (NSAID) or colchicine is often recommended during this period. During longer term maintenance use of urate lowering therapy, flares can also be precipitated by fluctuations in uric acid levels caused by non-adherence with prescribing instructions. Advantages of the current methods include decreasing the number, duration, frequency, or intensity of flares experienced by the patient (e.g. during initiation or maintenance of therapy for uric acid lowering), decreasing the need for dose titration, and reducing the amount or duration of additional anti-flare medicaments.

DETAILED DESCRIPTION

Figure 1:
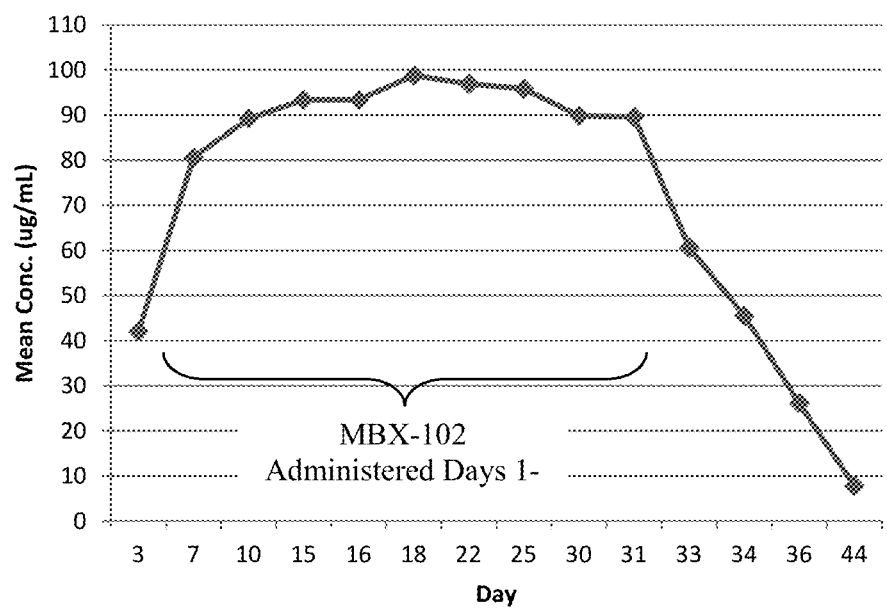
FIG. 1 is a graph showing the mean trough plasma concentration values of (−)-halofenic acid during and following a 30-day dosing schedule of daily oral administration of 400 mg of arhalofenate.

As utilized in accordance with the present disclosure, the following terms, unless otherwise indicated, shall be understood to have the following meanings:

"About" when qualifying a number, refers to a range of plus or minus ten percent of that value or number, unless indicated otherwise. Without limiting the application of the doctrine of equivalents as to the scope of the claims, each number should be construed in light of such factors as the number of reported significant digits and the manner or method (e.g. instrumentation, sample preparation, etc.) used to obtain that number.

"Administering" or "administration" refers to the act of giving a drug, prodrug, or therapeutic agent to a subject. Exemplary routes of administration are discussed below.

"Acute gout" refers to gout present in a subject with at least one gouty symptom (e.g., podagra or other gouty arthritis, gout flare, gouty attack).

"Chronic gout" refers to gout present in a subject having recurrent or prolonged gout flares, tophus formation, chronic inflammatory arthritis, or joint deterioration associated with gout, and includes the periods following recovery from acute gout and between acute gout attacks (i.e. intercritical gout).

"Composition" or, interchangeably, "formulation" refers to a preparation that contains a mixture of various excipients and key ingredients that provide a relatively stable, desirable, and useful form of a compound or drug.

The terms "combination therapy," "concomitantly administering" and "concomitant administration" refer to the administration of two or more agents in any manner in which the pharmacological effects of those agents are manifested in the subject at the same time. These terms encompass administering two or more agents to a subject substantially concurrently, for example in a single dosage form (e.g. a single capsule, pill, tablet, etc.), administering at least one agent in one dosage form and the other agent(s) in a separate dosage form, and administering each agent in its own separate dosage form. The administration may be performed sequentially or simultaneously. For example, for sequential administration, the first agent may be administered before or after the second agent.

The prefixes "d" and "l" or (+) and (−) are employed to designate the sign of rotation of plane-polarized light by the compound, with (+) or d-meaning that the compound is "dextrorotatory" and with (−) or l-meaning that the compound is "levorotatory". For a given chemical structure, these isomers or "optical isomers" are identical except that they are mirror images of one another. In describing an optically active compound, the prefixes R and S are used to denote the absolute configuration of the molecule about its chiral center(s). There is no correlation between the nomenclature for the absolute stereochemistry and for the rotation of an enantiomer (i.e., the R-isomer can also be the l-isomer). A specific optical isomer can also be referred to as an "enantiomer," and a mixture of such isomers is often called an "enantiomeric" or "racemic" mixture. See, e.g., A. Streitwiesser & C. H. Heathcock, INTRODUCTION TO ORGANIC CHEMISTRY, $2^{nd}$ Edition, Chapter 7 (MacMillan Publishing Co., U.S.A. 1981). The optical rotation $[\alpha]_D$ of (−)-halofenate was measured in methyl alcohol.

"Elevated serum uric acid level" refers to a serum uric acid level greater than normal and, in patients with gout, generally refers to a serum uric acid level greater than or equal to about 6 mg/dL. In some instances, elevated serum uric acid levels are above the mean level in a given population, such as those of a particular gender or age.

"Effective amount" refers to an amount required (i) at least partly to attain the desired response in a subject; (ii) to delay or to prevent the onset of a particular condition being treated in a subject; or (iii) or to inhibit or to prevent the progression of a particular condition being treated in a subject. The effective amount for a particular subject varies depending upon the health and physical condition of the subject to be treated, the taxonomic group of individual to be treated, the degree of protection desired, the formulation of the composition, the assessment of the medical situation, and other relevant factors. It is expected that the amount will fall in a relatively broad range that can be determined through routine trials.

"First urate-lowering agent" refers to a compound of any of Formula (I), (II), (III) or (IV) or a therapeutically acceptable salt or prodrug thereof. For clarity, this term implies no temporal aspect or relationship, e.g. to a second urate-lowering agent.

"Flare" or "gout flare" refers to a symptom of gout associated with a sudden onset of pain and inflammation, especially in peripheral joints such as the toes or fingers.

"Gout" refers to a group of disorders or symptoms most often associated with the accumulation of uric acid due to an overproduction of uric acid or a reduced ability of the kidney to excrete uric acid. Gout is often characterized by the deposition of urate crystals (uric acid or salts thereof, e.g. monosodium urate) in the joints (gouty arthropathy) or soft tissue (tophi). "Gout" as used herein includes acute gout, chronic gout, moderate gout, refractory gout and severe gout.

"Gout-associated inflammation" refers to local or systemic inflammation due to immune responses to the deposition of urate crystals.

"Halofenate" refers to compounds of Formula (III) below, i.e. (4-chlorophenyl)-(3-trifluoromethylphenoxy)-acetic acid 2-acetylaminoethyl ester (also referred to as the 2-acetamidoethyl ester of 4-chlorophenyl-(3-trifluoromethylphenoxy)-acetic acid). The term halofenate and the corresponding chemical names include both the (+) and (−) enantiomer of compounds of Formula (III) as well as mixtures thereof, unless otherwise specified.

"Halofenic acid" and "CPTA" refer to the compounds of Formula (IV), i.e. 4-chlorophenyl-(3-trifluoromethylphenoxy)-acetic acid [also referred to as 2-(4-chlorophenyl)-2-(3-(trifluoromethyl)phenoxy)acetic acid] as well as its pharmaceutically acceptable salts. The term halofenic acid and the corresponding chemical names include both the (+) and (−) enantiomer of compounds of Formula (IV) as well as mixtures thereof, unless otherwise specified.

"Hyperuricemia" refers to an elevated serum uric acid level (see above).

"Impaired renal function" refers to a medical condition in which the kidneys fail to adequately filter toxins and waste products from the blood. Impaired renal function may take the form or acute kidney injury or chronic kidney disease (i.e. CKD1-5).

"Moderate gout" refers to gout present in a subject having at least two gout flares in the past 12 months.

"Pharmaceutically acceptable" refers to that which is useful in preparing a pharmaceutical composition that is generally safe, non-toxic, and neither biologically nor otherwise undesirable, and includes that which is acceptable for veterinary or human pharmaceutical use.

"Pharmaceutically acceptable salt" includes pharmaceutically acceptable acid addition salts and pharmaceutically acceptable base addition salts and includes both solvated and unsolvated forms. Representative non-limiting lists of pharmaceutically acceptable salts can be found in S. M. Berge et al., *J. Pharma Sci.*, 66(1), 1-19 (1977), and *Remington: The Science and Practice of Pharmacy*, R. Hendrickson, ed., 21st edition, Lippincott, Williams & Wilkins, Philadelphia, Pa., (2005), at p. 732, Table 38-5, both of which are hereby incorporated by reference herein.

"Pharmaceutically acceptable acid addition salt" refers to salts formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to salts prepared from the addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

"Refractory gout" refers to gout in patients who are unresponsive or poorly responsive to one or more second urate-lowering agents, or have experienced or are at an increased risk of experiencing an adverse event therefrom. The terms "unresponsive" and "poorly responsive" in this context include (1) no or insignificant lowering of serum uric acid, (2) failure to reach a target serum uric acid level (e.g. as determined by a physician or other medical practitioner), and (3) the persistence of one or more gouty conditions or symptoms such as gout flares, gouty tophus, gouty arthritis, or other associated conditions regardless of any lowering of serum uric acid levels.

"Second urate-lowering agent" refers to a therapeutic agent that lowers serum uric acid levels that is not a first urate-lowering agent. Second urate-lowering agents include currently available agents (i.e. an agent approved by the FDA or other appropriate regulatory authority as of the filing date of this application) that lower serum uric acid, as well as compounds currently in development or under regulatory review. Examples of second urate-lowering agents are provided below. For clarity, this term implies no temporal aspect or relationship, e.g. to a first urate-lowering agent.

"Subject" and "patient" refer to animals such as mammals, including humans, other primates, domesticated animals (e.g. dogs, cats), farm animals (e.g. horses, cattle, goats, sheep, pigs), rats and mice.

"Severe gout" refers to gout present in a subject having tophaceous deposits in the joints, skin, or kidneys resulting in chronic arthritis, joint destruction, subcutaneous tophi, or kidney dysfunction, and, in some cases, with subsequent deformity and/or disability.

"Substantially free from" when used in reference to (−)-halofenate or (−)-halofenic acid (or a salt thereof) being substantially free from the corresponding (+) enantiomer (i.e. (+)-halofenate, (+)-halofenic acid, or a salt thereof) refers to a composition containing a high proportion of a compound's (−) enantiomer in relation to the (+) enantiomer. In one embodiment, the term means that by weight, the compound included in the composition is at least 85% (−) enantiomer and at most 15% (+) enantiomer. In one embodiment, the term means that by weight, the compound included in the composition is at least 90% (−) enantiomer and at most 10% (+) enantiomer. In other embodiments, the term means that by weight, the compound included in the composition is at least 91% (−) enantiomer and at most 9% (+) enantiomer, at least 92% (−) enantiomer and at most 8% (+) enantiomer, at least 93% (−) enantiomer and at most 7% (+) enantiomer, at least 94% (−) enantiomer and at most 6% (+) enantiomer, at least 95% (−) enantiomer and at most 5% (+) enantiomer, at least 96% (−) enantiomer and at most 4% (+) enantiomer, at least 97% (−) enantiomer and at most 3% (+) enantiomer, at least 98% (−) enantiomer and at most 2% (+) enantiomer, or at least 99% (−) enantiomer or greater than 99% (−) enantiomer. Other percentages of the (−) and (+) enantiomers may also be provided. These percentages are based upon the amount of the enantiomer relative to the total amount of both enantiomers of the compound in the composition.

"Therapeutically effective dose", "therapeutically effective amount", or, interchangeably, "pharmacologically acceptable dose" and "pharmacologically acceptable amount" mean that a sufficient amount of a therapeutic agent, therapeutic agents, or metabolites thereof will be present in order to achieve a desired result, e.g., lowering uric acid levels to a target goal or treating gout in its various forms or treating conditions associated with hyperuricemia.

"Treatment" and "treating" of a disease, disorder, condition or symptom refer to (1) preventing or reducing the risk of developing the disease, disorder or condition, i.e., causing the clinical symptoms of the disease, disorder or condition not to develop in a subject who may be exposed to or predisposed to the disease, disorder or condition but who does not yet experience or display symptoms of the disease, disorder or condition (i.e. prophylaxis); (2) inhibiting the disease, disorder or condition, i.e., arresting or reducing the development of the disease, disorder or condition or its clinical symptoms; and (3) relieving the disease, disorder or condition, i.e., causing regression, reversal, or amelioration of the disease, disorder or condition or reducing the number, duration, frequency or intensity one or more of its clinical symptoms (e.g. a gout flare). The term "management" may be used synonymously.

"Urate" refers to uric acid (7,9-dihydro-1H-purine-2,6,8 (3H)-trione) and ions and salts thereof.

This application describes methods of treating a gout flare comprising administering to the subject a compound of Formula (I)

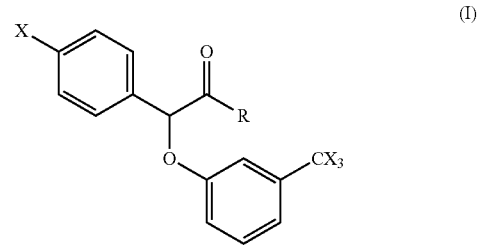

wherein R is selected from the group consisting of a hydroxy, lower aralkoxy, di-lower alkylamino-lower alkoxy, lower alkanamido-lower alkoxy, benzamido-lower alkoxy, ureido-lower alkoxy, N'-lower alkyl-ureido-lower alkoxy, carbamoyl-lower alkoxy, halophenoxy substituted lower alkoxy, carbamoyl substituted phenoxy, carbonyl-lower alkylamino, N,N-di-lower alkylamino-lower alkylamino, halo substituted lower alkylamino, hydroxy substituted lower alkylamino, lower alkanolyloxy substituted lower alkylamino, ureido, and lower alkoxycarbonylamino; and each X is independently a halogen, or a pharmaceutically acceptable salt thereof.

In certain aspects, the compound is a compound of Formula (II)

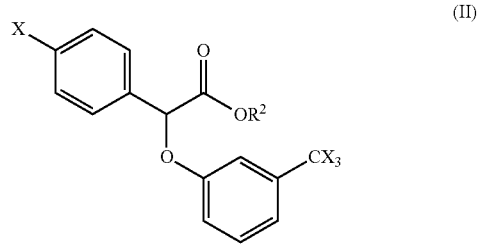

wherein $R^2$ is selected from the group consisting of phenyl-lower alkyl, lower alkanamido-lower alkyl, and benzamido-lower alkyl; and each X is independently a halogen, or a pharmaceutically acceptable salt thereof.

In other aspects, the compound is a compound of Formula (III), also referred to as halofenate

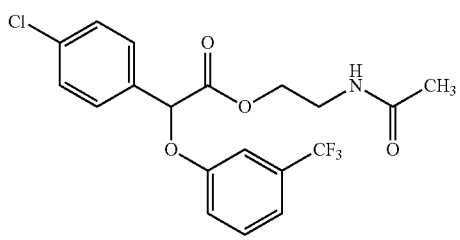

(III)

or a pharmaceutically acceptable salt thereof.

In other aspects, the compound is a compound of Formula (IV), also referred to as halofenic acid

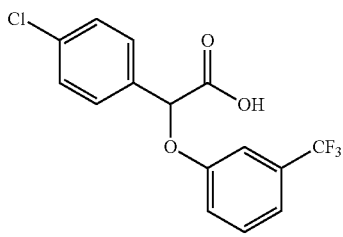

(IV)

or a pharmaceutically acceptable salt thereof.

It should be noted that any carbon atom with unsatisfied valences in the formulae and examples herein is assumed to have the hydrogen atom to satisfy the valences.

In certain embodiments the compound is a compound that generates the compound of Formula (IV) or a pharmaceutically acceptable salt thereof via a chemical reaction after being administered, as discussed in more detail below.

In certain embodiments, the compound is the (−) enantiomer of a compound of Formula (I), (II), (III) or (IV). In certain embodiments, the compound is (−)-halofenate (i.e. (−)-(R)-(4-chloro-phenyl)-(3-trifluoromethyl-phenoxy)-acetic acid 2-acetylamino-ethyl ester, also referred to as arhalofenate). In other embodiments, the compound is (−)-halofenic acid (i.e. (−)-4-chlorophenyl-(3-trifluoromethylphenoxy)acetic acid) or a pharmaceutically acceptable salt thereof. In certain embodiments, the (−)-halofenate, (−)-halofenic acid, or pharmaceutically acceptable salt thereof is substantially free from the corresponding (+) enantiomer.

The enantiomers (stereoisomers) of compounds of Formula (I), (II), (III) or (IV) and pharmaceutically acceptable salt thereof can be prepared by using reactants or reagents or catalysts in their single enantiomeric form in the process wherever possible or by resolving the mixture of stereoisomers by conventional methods including use of microbial resolution, resolving the diastereomeric salts formed with chiral acids or chiral bases and chromatography using chiral supports. See, also U.S. Pat. No. 7,199,259 (Daugs), U.S. Pat. Nos. 6,646,004; 6,624,194; 6,613,802; and 6,262,118 (each to Luskey et al.), U.S. Pat. No. 7,714,131 (Zhu et al.), U.S. Pat. No. 7,432,394 (Cheng et al.) and U.S. Publication No. 2010/0093854 (Broggini et al.) each of which are incorporated herein by reference in their entireties.

The chemical synthesis of racemic mixtures of (3-trihalomethylphenoxy) (4-halophenyl)acetic acid derivatives can also be performed by the methods described in U.S. Pat. No. 3,517,050, the teachings of which are incorporated herein by reference. The individual enantiomers can be obtained by resolution of the racemic mixture of enantiomers using conventional means known to and used by those of skill in the art. See, e.g., J. Jaques et al., in ENANTIOMERS, RACEMATES, AND RESOLUTIONS, John Wiley and Sons, New York (1981). Other standard methods of resolution known to those skilled in the art, including but not limited to, simple crystallization and chromatographic resolution, can also be used (see, e.g., STEREOCHEMISTRY OF CARBON COMPOUNDS (1962) E. L. Eliel, McGraw Hill; J. Lochmuller, *Chromatography* 113, 283-302 (1975)). Additionally, halofenate, halofenic acid, or a pharmaceutically acceptable salt thereof, i.e., the optically pure isomers, can be prepared from the racemic mixture by enzymatic biocatalytic resolution. Enzymatic biocatalytic resolution has been generally described previously (see, e.g., U.S. Pat. Nos. 5,057,427 and 5,077,217, the disclosures of which are incorporated herein by reference). Other generic methods of obtaining enantiomers include stereospecific synthesis (see, e.g., A. J. Li et al., *Pharm. Sci.* 86, 1073-1077 (1997)).

Figure 2:
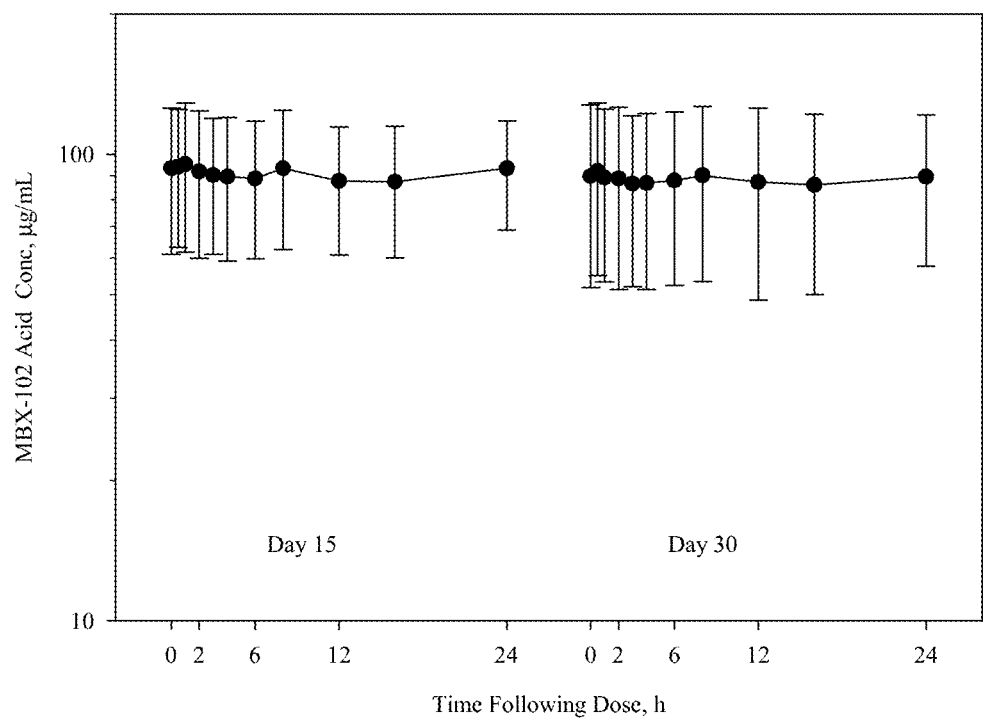
FIG. 2 is a graph showing the mean and standard deviation (SD) of (−)-halofenic acid plasma concentrations at Day 15 and Day 30 following daily oral administration of 400 mg of arhalofenate in 20 human subjects.
Figure 3:
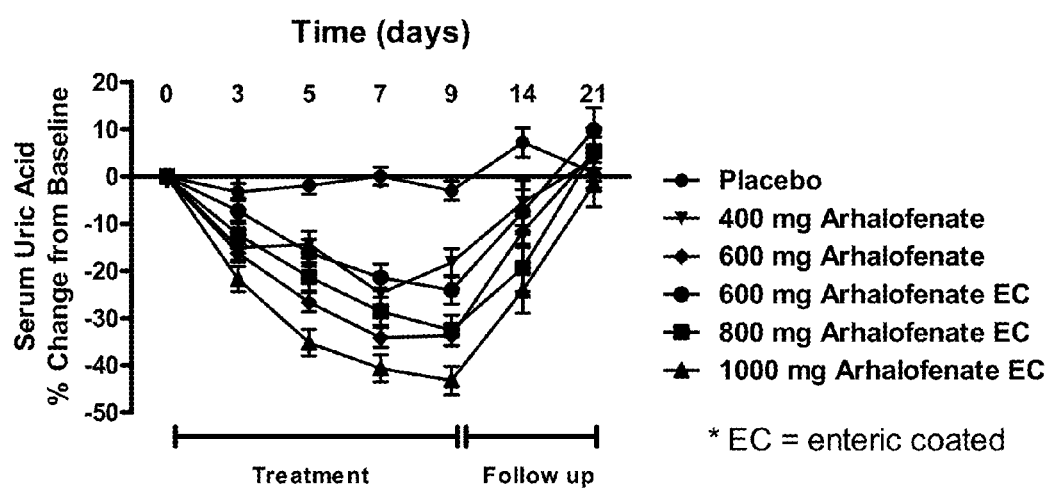
FIG. 3 is a graph showing reduction in serum uric acid in subjects over time following once daily dosing with arhalofenate.

FIGS. 1-2 show the pharmacokinetic profile of (−)-halofenic acid. FIG. 1 shows the mean trough plasma concentration values of (−)-halofenic acid during and following a 30-day dosing schedule of daily oral administration of 400 mg of arhalofenate. FIG. 2 shows the mean and standard deviation (SD) plasma concentration values of (−)-halofenic acid at day 15 and day 30 following daily oral administration of 400 mg of arhalofenate. These figures demonstrate a long half-life with sustained drug levels present for several days after the final dose, and a relatively constant intraday plasma concentration. The plasma concentration of (−)-halofenic acid is expected to correlate to the plasma concentration of uric acid. Accordingly, the long half-life and low intraday peak-to-trough ratio are expected to result in correspondingly gradual changes in serum uric acid during the initiation of and maintenance use of therapy. FIG. 3 demonstrates the reduction in serum uric acid over time with several doses of arhalofenate, and supports this theory. It is thought that large or rapid changes in serum uric acid (resulting from, for example, the administration of certain second urate-lowering agents, e.g. allopurinol, febuxostat, and others when no first urate-lowering agent is administered) can trigger gout flares or result in longer, more frequent, or more intense flares, for example during and for the several weeks and months after initiation of such agents, or with non-adherence to daily use of such agents. Therefore, the pharmacokinetic profile of (−)-halofenic acid should contribute to the successful use of compounds of Formula (I), (II), (III) or (IV) and pharmaceutically acceptable salts thereof in the prevention of gout flares (for example, during certain durations such as the first several weeks to month after initiation of administration), compared to other urate lowering therapies.

Methods described herein include reducing the number, duration, frequency or intensity of one or more gout flares, the methods comprising administering to a subject in need thereof a compound of any of Formula (I), (II), (III) or (IV) or a pharmaceutically acceptable salt thereof. In some embodiments the compound is (−)-halofenate, (−)-halofenic acid or a pharmaceutically acceptable salt thereof. In some embodiments, the number, duration, frequency or intensity of gout flares experienced by the subject is reduced relative to that experienced by the subject before such administration is initiated. In other embodiments, the number, duration, frequency or intensity of gout flares experienced by the subject is reduced relative to the number, duration, frequency or intensity of gout flares experienced by the subject when the subject has previously undergone urate-lowering therapy with a second urate-lowering agent. In some embodiments, the methods described herein are for the prevention of flares. In some embodiments, the methods described herein are for the prophylaxis of flares.

In certain methods described herein, a compound of Formula (I) and a flare prophylaxis or pain management agent (including, but not limited to, a non-steroidal anti-inflammatory drug (NSAID), an opiate, or colchicines, and wherein such agent is not a compound of Formula (I)) can be concomitantly administered to the subject. In certain methods, the amount or duration of administration of such flare prophylaxis or pain management agent is reduced (as compared to when no compound of Formula (I) is administered), and in other methods no such flare prophylaxis or pain management agent is administered.

The second urate-lowering agent may be any agent that lowers serum uric acid levels that is not a first urate-lowering agent (i.e. not a compound of any of Formula (I), (II), (III) or (IV) or a pharmaceutically acceptable salt thereof). These second urate-lowering agents include inhibitors of uric acid production (e.g. xanthine oxidase inhibitors and purine nucleoside phosphorylase inhibitors), uricosuric agents, and uricases. Xanthine oxidase inhibitors include, but are not limited to: allopurinol, febuxostat, oxypurinol, tisopurine, an inositol and propolis. In some embodiments, the xanthine oxidase inhibitor is allopurinol, febuxostat, oxypurinol, tisopurine, inositol, phytic acid, myo-inositiol, kaempferol, myricetin, and quercetin. Allopurinol (1,5-dihydro-4H-pyrazolo[3,4-d]pyrimidin-4-one), a xanthine oxidase inhibitor, is the current first line standard of care for lowering urate levels. Another xanthine oxidase inhibitor, febuxostat (2-(3-cyano-4-isobutoxyphenyl)-4-methyl-1,3-thiazole-5-carboxylic acid), was approved for treatment of gout in February 2009. Purine nucleoside phosphorylase (PNP) inhibitors represent a relatively new approach to lowering serum uric acid levels in patient with hyperuricemia, gout, and related conditions. In some embodiments, the PNP inhibitor is forodesine (BCX1777) (BioCryst Pharmaceuticals, Inc.). In other embodiments, the PNP inhibitor is ulodesine (BCX4208; 7-(((3R,4R)-3-hydroxy-4-(hydroxymethyl)pyrrolidin-1-yl)methyl)-3H-pyrrolo[3,2-d]pyrimidin-4(5H)-one) (BioCryst Pharmaceuticals, Inc.). Ulodesine monotherapy administered at 40, 80, 120, 160 and 240 mg/day has been shown to rapidly and significantly reduced serum uric acid in gout patients. Uricosuric agents enhance renal excretion of uric acid and generally act by lowering the absorption of uric acid from the kidney proximal tubule back to the blood, e.g., by inhibiting urate transporters, e.g, SLC22A12. Uricosuric agents include, but are not limited to, probenecid, 2-((5-bromo-4-(4-cyclopropylnaphthalen-1-yl)-4H-1,2,4-triazol-3-yl)thio) acetic acid (RDEA594, lesinurad), potassium 4-(2-((5-bromo-4-(4-cyclopropylnaphthalen-1-yl)-4H-1,2,4-triazol-3-yl)thio)acetamido)-3-chlorobenzoate (RDEA806), RDEA684, benzbromarone, sulfinpyrazone, amlodipine, atorvastatin, fenofibrate, guaifenesin, losartan, adrenocorticotropic hormone, and cortisone. Probenecid is the most commonly used uricosuric agent in the U.S. and may be given in combination with allopurinol to some gout patients. Benzbromarone and sulfinpyrazone are also used as first line uricosuric agents. Guaifenesin, losartan, atorvastatin, amlodipine, adrenocorticotropic hormone (ACTH or corticotropin), fenofibrate, levotofisopam, and cortisone also have uricosuric effects. Uricase or urate oxidase enzymes are found in many mammals but not humans. They can lower uric acid levels by converting uric acid into allantoin, a benign end metabolite which is easily excreted in the urine. Uricase enzymes include, but are not limited to, rasburicase or a pegylated uricase enzyme (PEG-uricase). In some embodiments, the pegylated uricase enzyme is Krystexxa® (PURICASE®; pegloticase) (Savient Pharmaceuticals, Inc.) which is approved in the U.S. for the treatment of chronic gout in adult patients refractory to conventional therapy.

In some embodiments, the number of gout flares experienced by the subject is reduced relative to the number, duration, frequency or intensity of gout flares experienced by the subject when the subject has previously undergone urate-lowering therapy with a second urate-lowering agent, wherein the second urate-lowering agent is allopurinol, febuxostat, lesinurad or BCX4208.

Certain methods provide for the treatment or management of hyperuricemia in a subject with gout and reducing the number, duration, frequency or intensity of gout flares experienced by the subject. These methods comprise administering to a subject in need thereof a compound of any of Formula (I), (II), (III) or (IV) or a pharmaceutically acceptable salt thereof. In some embodiments the compound is (−)-halofenate, (−)-halofenic acid or a pharmaceutically acceptable salt thereof.

Figure 4:
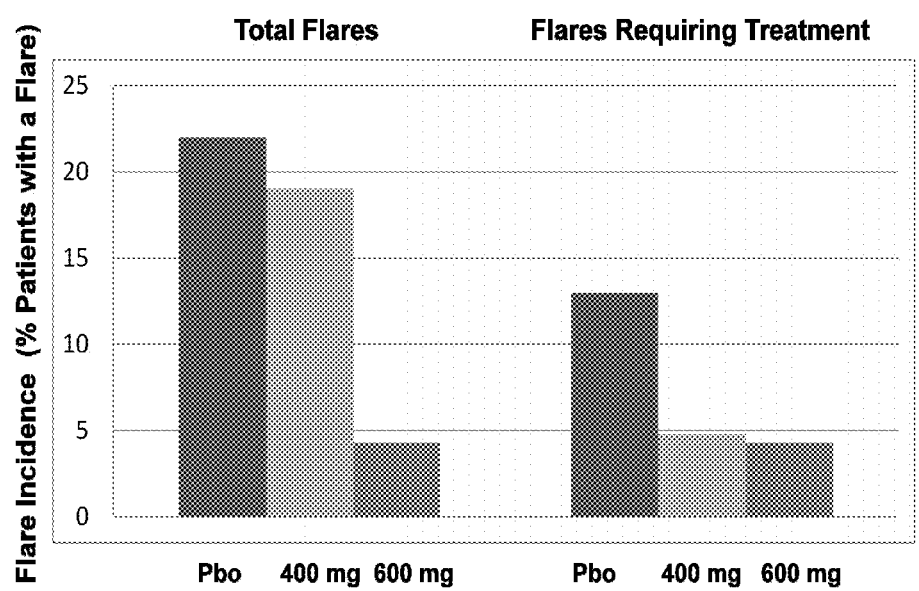
FIG. 4 is a chart showing the effect of the administration of (−)-halofenate on the incidence of gout flares in human subjects. "Pbo" means placebo; dosage information refers to the daily dosage of (−)-halofenate.
Figure 5:
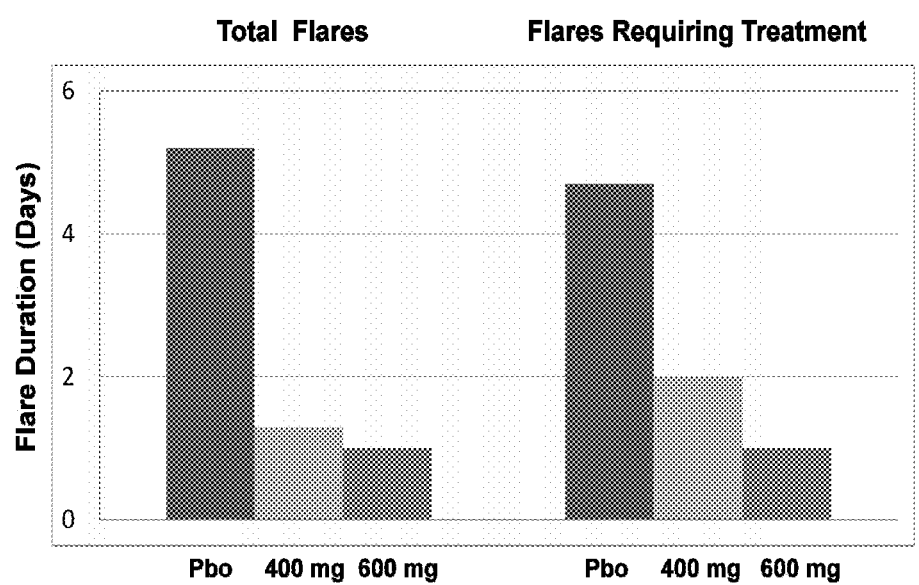
FIG. 5 is a chart showing the effect of the administration of (−)-halofenate on flare duration in human subjects. "Pbo" means placebo; dosage information refers to the daily dosage of (−)-halofenate.

FIGS. 4-5 show the effect of (−)-halofenate monotherapy on gout flares in human subjects. Referring to FIG. 4, the administration of (−)-halofenate dose dependently reduced the incidence of any flares (Total flare) and flares requiring treatment compared to placebo (presented as percentage of patients experienced any flares (total flare) and flares requiring treatment by treatment arm). Referring to FIG. 5, the administration of (−)-halofenate also reduced the duration of all flares (any flares and flares requiring treatment). See Example below for more details.

Figure 6:
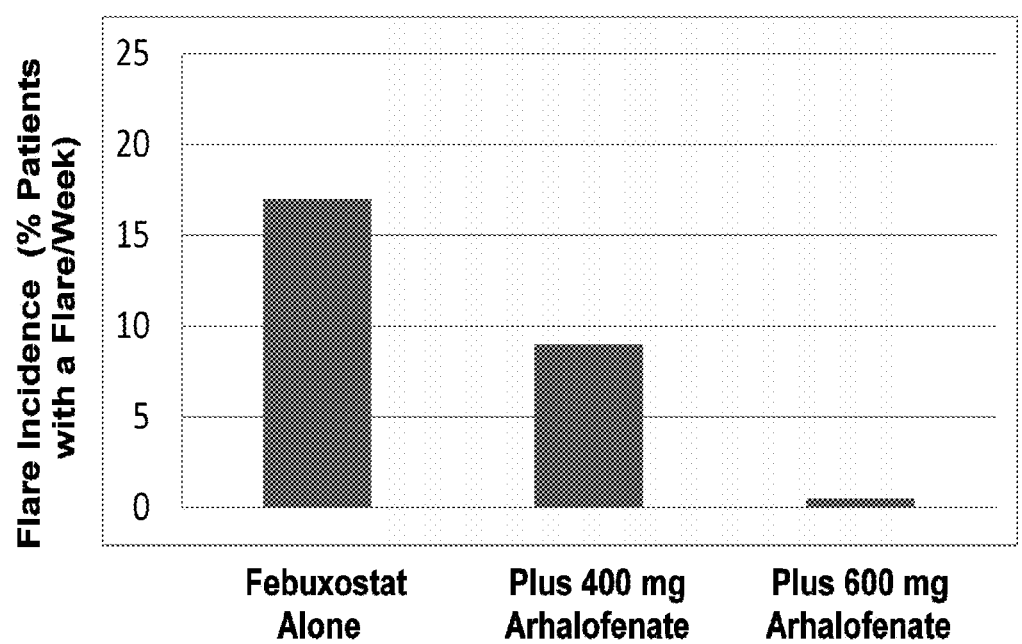
FIG. 6 is a chart showing the effect of febuxostat alone and concomitant administration of febuxostat and (−)-halofenate on the incidence of gout flares in human subjects presented as percentage of patients experienced any flare per week.
Figure 7:
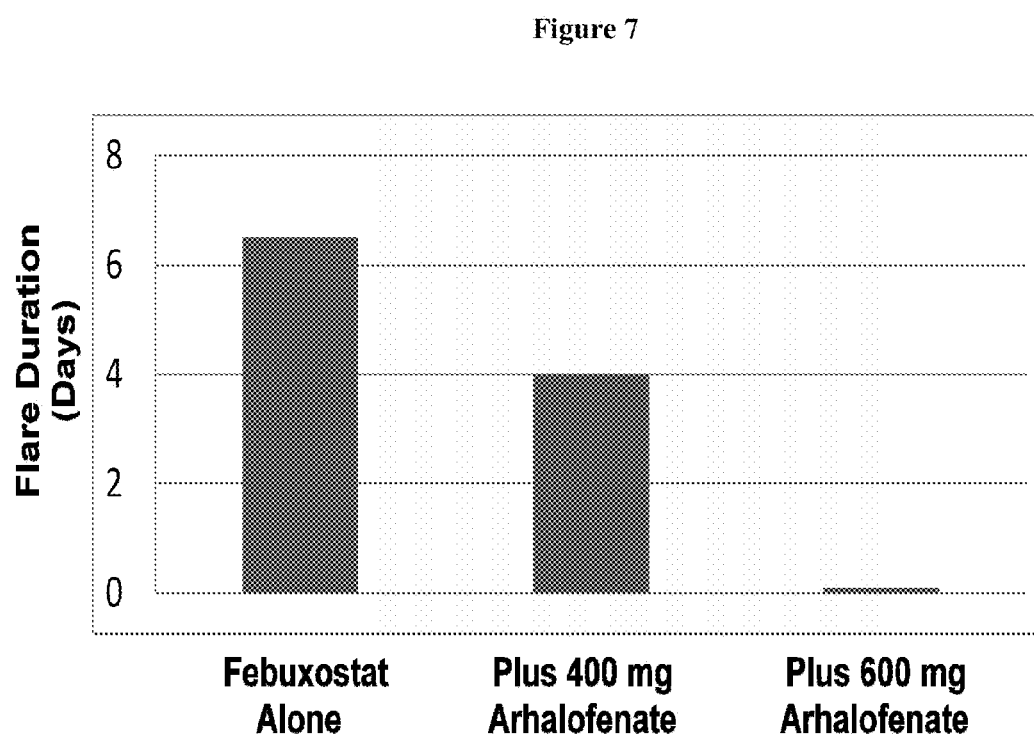
FIG. 7 is a chart showing the effect of febuxostat alone and concomitant administration of febuxostat and (−)-halofenate on flare duration in human subjects.

FIGS. 6-7 show the effect of concomitant administration of (−)-halofenate with febuxostat (a second urate-lowering agent, as described herein), compared to the administration of febuxostat with no other urate-lowering agent ("Febuxostat Alone") on gout flares in human subjects. Referring to FIG. 6, the concomitant administration of (−)-halofenate and febuxostat reduced flare incidence as compared to the administration of febuxostat without (−)-halofenate. FIG. 7 shows that such concomitant administration also reduced the duration of flares. See Example below for more details.

In various embodiments, the methods described herein lower serum uric acid levels in a subject by about 5%, about 10%, about 15%, about 20%, about 25%, about 30%, about 35%, about 40%, about 45%, about 50%, about 55%, about 60%, about 65%, about 70%, about 75%, about 80%, about 85%, about 90% or more, as compared to serum uric acid levels in the subject prior to administering the methods described herein. In various embodiments, serum uric acid levels are decreased about 5% to about 50%, decreased by about 25% to about 75%, or decreased by about 50% to about 99%. Methods to determine serum uric acid levels are well known in the art and are often measured as part of a standard chemistry panel of blood serum samples.

In some embodiments, the methods of the present disclosure lower serum uric acid levels in a subject to about 7 mg/dL or less, to about 6.5 mg/dL or less, to about 6 mg/dL or less, to about 5 mg/dL or less, to about 4 mg/dL or less, or to about 3 mg/dL or less as compared to serum uric acid levels in the subject prior to administering the methods or compositions described herein. In some embodiments, the methods of the present disclosure lower serum uric acid levels in a subject by 0.1, 0.2, 0.3, 0.4, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 or 10.0 mg/dL, or greater, as compared to serum uric acid levels in the subject prior to administering the methods or compositions described herein. In further embodiments, the methods described herein lower serum uric acid levels by between 0.1 and 10.0 mg/dL, between 0.5 and 6.0 mg/dL, between 1.0 and 4.0 mg/dL or between 1.5 and 2.5 mg/dL. The appropriate serum uric acid level may vary depending on the subject, and may vary for a given subject over time, depending upon the subject's overall medical condition. Similarly, the appropriate serum uric acid level for one group of subjects sharing a common medical condition may be different from that which is appropriate for a different group of subjects sharing a different medical condition. Thus, it may be advisable to reduce the serum uric acid level of a given group of subjects to, for example, below about 5 mg/dL, and to reduce the serum uric acid level of a different group of subjects to, for example, below about 4 mg/dL. In certain embodiments, the methods of the present disclosure decrease a serum uric acid level in the subject by an amount sufficient to result in the disappearance, reduction, amelioration, or the prevention of the onset, of one or more conditions associated with elevated serum uric acid over a certain timeframe, for example about a week, about a month, about six months, about one year, about two years, or for a longer duration. For example, a method can decrease the serum uric acid level in a subject by an amount sufficient to result in the disappearance or reduction of tophi over about one week, about one month, about six months, about one year, about two years, or longer, e.g. indefinitely, e.g. for the remainder of the lifetime of the subject.

In further embodiments, the methods of the present disclosure comprise administering a pharmaceutical composition comprising a compound of Formula (I), (II), (III) or (IV) or a pharmaceutically acceptable salt thereof to a subject whose serum uric acid level is at least about 4 mg/dL, at least about 5 mg/dL, at least about 6 mg/dL, at least about 6.8 mg/dL, at least about 7 mg/dL, at least about 8 mg/dL, at least about 9 mg/dL, at least about 10 mg/dL, or at least about 11 mg/dL. Again, the amount of decrease of serum uric acid level that is appropriate may vary depending on the subject, depending upon the subject's overall medical condition. Similarly, the amount of decrease of serum uric acid level that is appropriate for one group of subjects sharing a common medical condition may be different from that which is appropriate for a different group of subjects sharing a different medical condition.

The methods described herein (as well as the underlying physiological mechanisms related to them) may be accomplished by the administration of a compound that generates the compound of Formula (IV) or a salt thereof via a chemical reaction after being administered. Such compounds include prodrugs of the compound of Formula (IV). Prodrugs of a compound are prepared by modifying functional groups present in the compound in such a way that the modifications may be cleaved in vivo to release the parent compound, or an active metabolite. For example, prodrugs include compounds wherein a hydroxy, amino or sulfhydryl group in a compound is bonded to any group that may be cleaved in vivo to regenerate the free hydroxyl, amino, or sulfhydryl group, respectively. Certain prodrugs may increase the bioavailability of the compounds of the embodiments when such compounds are administered to a subject (e.g., by allowing an orally administered compound to be more readily absorbed into the blood) or which enhance delivery of the parent compound to an organ or tissue (e.g., adipose tissue, kidneys, liver, muscle, or joints) relative to the parent species. More particularly, prodrugs of the compound of Formula (IV) include esters, amides, and carbamates (e.g., N,N-dimethylaminocarbonyl) of the hydroxy functional group of the compound of Formula (IV). The compounds of Formulae (I), (II) and (III) are non-limiting examples of prodrugs of the compound of Formula (IV). Further examples of prodrugs can be found in J. Rautio et al. *Prodrugs: design and clinical applications*, Nat. Rev. Drug Discov., 7, 255-270 (2008); Edward B. Roche, ed., *Bioreversible Carriers in Drug Design*, American Pharmaceutical Association and Pergamon Press, (1987); and T. Higuchi and V. Stella, *Pro-drugs as Novel Delivery Systems*, Vol. 14 of the A.C.S. Symposium Series (1975), each of which are hereby incorporated by reference herein.

The compounds of Formulae (I), (II), (III) and (IV) and pharmaceutically acceptable salts thereof are contemplated to exhibit therapeutic activity when administered in an amount which can depend on the particular case. The variation in amount can depend, for example, on the subject being treated and the active ingredients chosen. A broad range of doses can be applicable. Dosage regimes may be adjusted to provide the optimum therapeutic response. For example, several divided doses may be administered daily, weekly, monthly or other at suitable time intervals or the dose may be proportionally reduced as indicated by the exigencies of the situation. Such dosages are optionally altered depending on a number of variables, not limited to the activity of the one or more active ingredients used, the disease or condition to be treated, the mode of administration, the requirements of the individual subject, the severity of the disease or condition being treated, and the judgment of the practitioner.

Depending on factors such as the diagnosis, symptoms, and therapeutic goals of a particular subject, a wide range of dosages of the compound of Formula (I), (II), (III) or (IV) can be contemplated. In various embodiments, the compound may be administered from about 10 mg to about 1000 mg per day. For example, halofenate, halofenic acid, or a pharmaceutically acceptable salt thereof may be administered at about 50 mg/day, about 100 mg/day, about 200 mg/day, about 300 mg/day, about 400 mg/day, about 500 mg/day, about 600 mg/day, about 700 mg/day, about 800 mg/day, about 900 mg/day, or about 1000 mg/day.

Dose titration or dose escalation protocols may be employed to determine the proper or optimal dose to administer to a subject. For example, dose titration or escalation studies may select for doses that improve efficacy or tolerability. Dose titration or escalation allows for the gradual adjusting of the dose administered until the desired effect is achieved. Dose titration gradually decreased the dosage administered while dose escalation gradually increases the dose administered. Methods of dose titration and escalation are well known in the art. As a non-limiting example, a subject may be administered 200 mg/day halofenate, halofenic acid, or a pharmaceutically acceptable salt thereof every day and measured for serum uric acid levels on a daily basis. The dosage may be increased or decreased, for example, on a weekly basis. The subject may be monitored for a period of, for example, 2 to 12 weeks to find the desired dose.

Compounds of Formula (I), (II), (III) or (IV) can be incorporated into a variety of formulations and medicaments for therapeutic administration. More particularly, these compounds can be formulated into pharmaceutical compositions or formulations by combination with appropriate, pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, or intratracheal administration. Moreover, the compound can be administered in a local rather than systemic manner, in a depot or sustained release formulation. In addition, the compounds can be administered in a liposome.

Compounds of Formula (I), (II), (III) or (IV) or a pharmaceutically acceptable salt thereof can also be formulated with common excipients, diluents or carriers and compressed into tablets, or formulated as elixirs or solutions for convenient oral administration, or administered by the intramuscular or intravenous routes. The compounds can be administered transdermally, and can be formulated as sustained release dosage forms and the like. In one embodiment, the above methods may further comprise the administration of a second urate-lowering agent selected from the group consisting of a xanthine oxidase inhibitor, an inhibitor of uric acid production, a uricosuric agent and a uricase. In one embodiment, the method comprise administering a pharmaceutical composition comprising a first urate-lowering agent and a second therapeutic agent, as described herein, to a subject whose serum uric acid level is at least about 4 mg/dL, at least about 5 mg/dL, at least about 6 mg/dL, at least about 6.8 mg/dL, at least about 7 mg/dL, at least about 8 mg/dL, at least about 9 mg/dL, at least about 10 mg/dL, or at least about 11 mg/dL. The amount of decrease of serum uric acid level that is appropriate may vary depending on the subject, depending upon the subject's overall medical condition. Similarly, the amount of decrease of serum uric acid level that is appropriate for one group of subjects sharing a common medical condition may be different from that which is appropriate for a different group of subjects sharing a different medical condition.

In other embodiments, a first and a second urate-lowering agent (wherein these first and second urate-lowering agents are described herein) can be concomitantly administered. Such administration does not require that a single pharmaceutical composition, the same type of formulation, the same dosage form, or even the same route of administration be used for administration of both the first and second urate-lowering agents, or that the two agents be administered at the same time. Such administration may be accomplished by the same dosage form and the same route of administration, at substantially the same time. For example, a first urate-lowering agent, e.g. halofenate, halofenic acid, or a pharmaceutically acceptable salt thereof, and a second urate-lowering agent, e.g. xanthine oxidase inhibitor (e.g., allopurinol or febuxostat), can be administered to the subject together in a single oral dosage composition, such as a tablet or capsule, or each agent can be administered in separate oral dosage formulations. One advantage with separate formulations is an added flexibility in dosing, i.e., the dosage of the first and second urate-lowering agents can be changed independently, quickly, and easily. Where separate dosage formulations are used, the first and second urate-lowering agents can be administered at essentially the same time (i.e., simultaneously or concurrently), or different times (i.e., sequentially). In various embodiments, the second urate-lowering agent can be administered at from about 10 mg to about 4000 mg per day. In certain embodiments, the second urate-lowering agent is a xanthine oxidase inhibitor, preferably selected from the group consisting of allopurinol, febuxostat, oxypurinol, tisopurine, inositol, phytic acid, myo-inositiol, kaempferol, myricetin, and quercetin, especially allopurinol or febuxostat. In certain embodiments, the second urate-lowering agent is allopurinol and is administered at from about 50 mg to about 800 mg per day. In other embodiments, the second urate-lowering agent is febuxostat and is administered at from about 40 mg to about 120 mg per day. For example, in certain embodiments, the first urate-lowering agent is (−)-halofenate and is administered at from about 100 mg to about 1000 mg per day, and the second urate-lowering agent is febuxostat and is administered at from about 40 mg to about 120 mg per day. By way of further non-limiting examples wherein the first urate-lowering agent is (−)-halofenate and wherein the second urate-lowering agent is febuxostat, the following daily dosages may be administered: arhalofenate 600 mg/day, febuxostat 40 mg/day; arhalofenate 600 mg/day, febuxostat 80 mg/day; arhalofenate 600 mg/day, febuxostat 120 mg/day; arhalofenate 800 mg/day, febuxostat 40 mg/day; arhalofenate 800 mg/day, febuxostat 80 mg/day; arhalofenate 800 mg/day, febuxostat 120 mg/day. In another embodiment, the second urate-lowering agent is a uricosuric agent, preferably selected from the group consisting of probenecid, 2-((5-bromo-4-(4-cyclopropylnaphthalen-1-yl)-4H-1,2,4-triazol-3-yl)thio) acetic acid, potassium 4-(2-((5-bromo-4-(4-cyclopropylnaphthalen-1-yl)-4H-1,2,4-triazol-3-yl)thio)acetamido)-3-chlorobenzoate, RDEA684, benzbromarone, sulfinpyrazone, amlodipine, atorvastatin, fenofibrate, guaifenesin, losartan, adrenocorticotropic hormone and cortisone, especially probenecid.

Other dose ranges within the ranges described above for each of the first urate-lowering agent and the second urate-lowering agent may be readily envisaged. One of skill in the art will appreciate that the dose and dosing regimen may be adjusted when therapeutic agents are used in combination. When such combinations are used, the dose of one or more of the agents may be reduced to a level below the level required for a desired efficacy when the one or more agents are used alone. Similarly, the dosing regimen may be modified, e.g., to synchronize the dosing of the one or more therapeutic agents to facilitate improved patient ease of use and compliance. Alternately, the dosing regimen of the one or more therapeutic agents can be sequential, e.g., to reduce the combined load of the agents at a given time. For example, in certain embodiments, the dose of the second urate-lowering agent (e.g. allopurinol, febuxostat, or the other second urate-lowering agents described herein) can be adjusted to a lower level than that currently recommended when the first urate-lowering agent is and second urate-lowering agents are administered.

In various embodiments, compounds of Formula (I), (II), (III) or (IV) or a pharmaceutically acceptable salt thereof can be administered over a broad frequency range. For example, in various embodiments the compounds may be administered once daily (QD), twice daily (BID), three times daily (TID) or four times per day (QID). In one embodiment, the compound is administered once daily (QD). In another embodiment, the compound is administered twice daily (BID). In other embodiments, administration of the compound can be skipped without having deleterious effect, that is, the compound can be administered over (i.e. before and after) a "drug holiday" where the drug holiday is the period of the skipped dose. For example, in a daily dosing regimen, the compound can be administered over a drug holiday of one day, (i.e. administered on day N and day N+2 but not on day N+1, where day N is any arbitrary day) without the subject experiencing any substantially or materially adverse effect from the skipped administration. In certain embodiments the drug holiday can be two days. In other embodiments the drug holiday can be more than two days.

In various embodiments, compounds of Formula (I), (II), (III) or (IV) or a pharmaceutically acceptable salt thereof can be administered over a broad duration. For example, in various embodiments the compounds may be administered for about 10 days or longer, about four weeks or longer, about one month or longer, about 12 weeks or longer, about three months or longer, about six months or longer, about one year or longer, about two years or longer, about five years or longer, or about 10 years or longer. In some embodiments the administration may be indefinite, e.g. for the remainder of the lifetime of the subject.

The pharmacokinetic profile of (−)-halofenic acid can be modulated by the dose, frequency, and duration of administration of the compound or a prodrug thereof. One measure of the pharmacokinetic profile is the peak-to-trough ratio, defined as the highest blood plasma concentration divided by the lowest blood plasma concentration of a compound or agent within a certain time interval (e.g. within the interval corresponding to the frequency of administration). For example, certain methods include providing to a subject an intraday peak-to-trough ratio of (−)-halofenic acid of about 2.0 or less, comprising administering to the subject a compound of Formula (I), (II), (III) or (IV) or pharmaceutically acceptable salts thereof at a dose of about 100 to about 1000 mg per day. In various embodiments, the intraday peak-to-trough ratio is about 1.7 or less, about 1.5 or less, about 1.4 or less, or about 1.3 or less. In embodiments, the intraday peak-to-trough ratio is provided after administering the compound daily for at least about 10 days, e.g. at least about 12 days. The pharmacokinetic profile can also depend on the route of administration, as well as by the compound and formulation administered to the subject. For example, one method includes providing to a subject an intraday peak-to-trough ratio of (−)-halofenic acid of about 2.0 or less, comprising administering to the subject arhalofenate (i.e. (−)-halofenate) by mouth in an oral formulation (e.g. a tablet, capsule, pill, etc. as described above) at a dose of 100 to 1000 mg per day.

Certain methods described herein may be accomplished by administering a compound of Formula (I), (II), (III) or (IV) or pharmaceutically acceptable salts thereof at a certain dose, frequency, and duration of administration, as provided herein. For example, certain methods provide for the treatment of hyperuricemia in a subject with gout comprising administering to a subject in need thereof a compound of Formula (I), (II), (III) or (IV) or pharmaceutically acceptable salts thereof wherein the dose, frequency, and duration of administration are effective to reduce the number, duration, frequency, or intensity of gout flares experienced by the subject during the duration of administration. In some embodiments, the compound is arhalofenate. In some embodiments the dose is from about 100 mg to about 1000 mg. In some embodiments the frequency is daily. In some embodiments the duration of administration is about 10 days or longer, about four weeks or longer, about one month or longer, about 12 weeks or longer, about three months or longer, about six months or longer, about one year or longer, about two years or longer, about five years or longer, or about 10 years or longer. In some embodiments the administration may be indefinite, e.g. for the remainder of the lifetime of the subject. In some embodiments the administration daily and over a drug holiday of one day. In some embodiments further comprise administering to the subject arhalofenate by mouth in an oral formulation. Particular embodiments covering compositions, formulations and their method of uses are disclosed in a PCT Patent Application No. PCT/US11/59394 entitled "Methods for Treating Hyperuricemia in Patients with Gout Using Halofenate or Halofenic Acid and a Second Urate-Lowering Agent" filed Nov. 4, 2011, and the PCT Application is incorporated herein in its entirety.

In other aspects, the compounds and methods described herein may be used to treat or prevent familial Mediterranean fever; thrombocytopenic purpura; pericarditis; scleroderma; Behcet's disease; rheumatoid arthritis; familial cold autoinflammatory syndrome; Muckle-Wells syndrome; chronic infantile neurologic, cutaneous and articular syndrome/neonatal onset multisystem inflammatory disease (CINCA/NOMID); pyogenic arthritis, pyoderma gangrenosum and acne (PAPA), and related disorders.

Methods

Methods used in relation to FIGS. 1-2 showing the pharmacokinetic profile of (−)-halofenic acid were as follows:

Plasma proteins in human plasma samples containing of (−)-halofenic acid, an internal standard (I.S.) and heparin as the anticoagulant were precipitated with acetonitrile. The samples were vortex mixed, centrifuged and an aliquot was analyzed by reversed phase high performance liquid chromatography using a Phenomenex Polar RP column maintained at 45° C. The mobile phase was nebulized using heated nitrogen in a Z-spray source/interface and the ionized compounds were detected using a tandem quadrupole mass spectrometer.

The plasma concentrations were rounded to the nearest one-tenth μg/mL before the calculations. Plasma samples with concentrations below the quantifiable limit of 1.0 μg/mL (BQL) were assigned values of zero.

Methods used in relation to FIG. 3 showing reduction in serum uric acid in subjects over time following once daily dosing with arhalofenate were as follows.

A single centre Phase 1, placebo- and positive-controlled, double-blind, randomized, dose escalation study was conducted to evaluate the multiple-dose pharmacokinetics (PK) of (−)-halofenate administered as a daily dose orally for 10 days, at the protocol-specified doses in healthy adult subjects. A total of 119 subjects completed study treatment according to protocol: 6 subjects received (−)-halofenate 100 mg/day for 10 days; 6 subjects received (−)-halofenate 200 mg/day for 10 days; 9 subjects received (−)-halofenate 400 mg/day for 10 days; 20 subjects received (−)-halofenate 600 mg/day for 10 days; 10 subjects received (−)-halofenate 600 mg Enteric Coated (EC)/day for 10 days; 9 subjects received (−)-halofenate 800 mg EC/day for 10 days; 10 subjects received (−)-halofenate 1000 mg EC/day for 10 days; 24 subjects received placebo treatment daily for 10 days; and 25 subjects received naproxen 500 mg b.i.d. monotherapy for 7 days. In this study, serum uric acid was measured at screening and on Days 1, 3, 5, 7, 9, 14 and 21.

TABLE 1

| Treatment group | N | Mean uric acid at baseline (mg/dL) | Mean uric acid at Day 9 (mg/dL) | Mean change at Day 9 (mg/dL) | Mean % change |
|---|---|---|---|---|---|
| Placebo | 23 | 4.70 | 4.66 | −0.04 | −1 |
| 400 mg | 10 | 4.91 | 3.89 | −1.02 | −21 |
| 600 mg | 20 | 5.04 | 3.40 | −1.65 | −33 |
| 600 mg EC | 10 | 5.61 | 3.92 | −1.69 | −30 |
| 800 mg EC | 9 | 5.60 | 3.83 | −1.77 | −32 |
| 1000 mg EC | 10 | 5.48 | 3.04 | −2.44 | −45 |

As shown in FIG. 3 and Table 1, data from this study demonstrates that the treatment with (−)-halofenate resulted in gradual reduction in serum uric acid over a period of time at all dose levels tested, and in a dose dependent manner.

EXAMPLES

Example 1

Suppression of Uric-Acid Induced Inflammation In Vitro

Differentiated murine 3T3-L1 adipocytes are cultured in vitro in 24 well plates. To the culture medium (−)-halofenic acid is added at a final concentration of 50-150 μM prior to the addition of uric acid at 5 mg/dL or 15 mg/dL and the culture continued for 3 or 7 days. A parallel culture of cells is conducted in the presence of a vehicle such as dimethylsulfoxide (DMSO). At the end of the culture period media is removed, cells are isolated and messenger RNA prepared. The levels of secreted cytokines representing a panel of pro-inflammatory cytokines including but not restricted to monocyte chemoattractant protein-1 (MCP-1), tumor necrosis factor α (TNF-α), interleukin-1β, (IL-1β), interleukin-6 (IL-6) and interleukin-12 (Il-12) are determined in the media isolated from the cells using commercially available cytokine assay kits. The levels of gene expression for the mRNAs for a panel of pro-inflammatory cytokines including but not restricted to monocyte chemoattractant protein-1 (MCP-1), tumor necrosis factor α (TNF-α), interleukin-1β, (IL-1β), interleukin-6 (IL-6) and interleukin-12 (Il-12) are determined using real-time PCR. The addition of (−)-halofenate prevents the uptake of uric acid into 3T3-L1 adipocytes and thereby suppresses the uric acid induced inflammatory response resulting in a reduced level of expression and consequently secretion of this panel of pro-inflammatory cytokines. A similar study is also conducted in primary mouse macrophages and human umbilical vein endothelial cells.

Example 2

Animal Gout Hare Model

The models described in R. Torres et al., Ann Rheum. Dis. 68, 1602-08 (2009) (available at http://ard.bmj.com/content/68/10/1602.long), which is herein incorporated by reference in its entirety, is used. Briefly, twenty C57BL6 mice are obtained from Jackson Laboratories (Bar Harbor Me. USA) and used between the ages of 12 and 16 weeks. The mice are housed singly at least a week before study and allowed access to regular chow and water ad libitum. Arhalofenate is administered orally to half (ten) of the mice (test mice) daily at a dose of 125 mg/kg for periods of time including for example 1 day, 5 days and 2 weeks prior to induction of inflammation by uric acid. The remaining ten mice (control mice) are administered a vehicle consisting of 1% Carboxymethyl Cellulose//2% Tween-80. In another treatment modality, arhalofenate is co-administered at the time of uric acid treatment.

Crystals of monosodium urate (MSU) are prepared as described in R. Liu-Bryan et al., Arthritis Rheum. 52, 2936-46 (2005). In one model, MSU crystals (0.5 mg) suspended in 20 microliters of endotoxin-free PBS are injected intro-articularly into the tibio-tarsal joint (ankle) of the mice anaesthetized with 2.5% isoflurane. Thermal hyperalgesia, weight bearing ability, angle joint diameter, and histological analyses are performed according to Torres et al, supra. The level of secretion of a panel of pro-inflammatory cytokines including but not restricted to monocyte chemoattractant protein-1 (MCP-1), tumor necrosis factor α (TNF-α), interleukin-1β, (IL-1β), interleukin-6 (IL-6) and interleukin-12 (Il-12) are measured in fluid isolated from the injected joints. Joints are dissected and homogenized to allow preparation of mRNA and the level of gene expression of the same panel of pro-inflammatory cytokines determined. In another model, mice are injected intraperitoneally with 1 mg of MSU suspended in 0.5 ml of endotoxin free PBS. After 6 h, mice are killed and their peritoneal cavities washed and harvested for measurement of neutrophil influx by staining with a neutrophil specific antibody R-phycoerythrin conjugated rat anti mouse Ly-6G monoclonal antibody. In another model, an air pouch is introduced subcutaneously and 1 mg of MSU is injected into the pouch. Six hours after crystal injection the cells resident in the pouch are collected by lavaging with 5 ml of buffer. Neutrophil infiltration is measured by staining as above. The levels of monocyte chemoattractant protein-1 (MCP-1), tumor necrosis factor α (TNF-α), interleukin-1β, (IL-1β), interleukin-6 (IL-6) and interleukin-12 (Il-12) are also measured in the lavaged fluid isolated from the urate injected air pouch.

Example 3

Clinical Trial Evaluating the Effectiveness of Arhalofenate at the Doses of 400 mg and 600 mg Compared to Placebo in Serum Uric Acid Reduction and Flare Prevention in Gout Patients with Hyperuricemia Study Design: This was a randomized, double-blind, placebo-controlled study of 400 mg and 600 mg arhalofenate administered daily for 4 weeks as monotherapy in patients with gout (per criteria of the American Rheumatism Association) with hyperuricemia. Patients using urate lowering therapy (ULT) must have been willing to discontinue treatment for the duration of the study. Patients with a recent history of an acute gout flare must have been symptom free for at least 1 week prior to screening.

Upon successful completion of screening, patients entered into a minimum 3-week Run-in/Stabilization Phase. During this phase, patients on existing ULT were asked to temporarily discontinue their current therapy. Patients also started colchicine 0.6 mg once daily until the final study visit as prophylaxis to prevent potential gout flares. Patient who met final eligibility criteria were randomized (1:1:1) into the Treatment Phase to receive Placebo, arhalofenate 400 mg, or arhalofenate 600 mg. Each randomized patient took double-blind study medication daily for a period of four weeks beginning at Day 1 (Visit 3). Patients returned to the study site after 2 weeks at Visit 4 and then weekly at Visits 5 and 6 (Weeks 3 and 4). A Follow-up Visit (Visit 7) took place 2 weeks after the last dose of study medication.

Diagnosis and Main Criteria for Inclusion: Male or female patients aged 18 to 75 years, inclusive who had been diagnosed with gout and had an sUA≥8.0 mg/dL and ≤12.0 mg/dL were eligible to participate in this study. Patients with a recent history of an acute gout flare must have been symptom free for at least 1 week prior to both screening and randomization.

Criteria for Evaluation:

The primary efficacy analysis compared the percentage change in sUA from baseline to end of treatment between the treatment groups. In addition, gout flares were captured as special interest event and the incidence of gout flares (all flares and flares that required treatment), severity (as assessed either mild, moderate, or severe by the Principal Investigator), and duration (days) were compared between treatment groups.

Results:

All randomized patients in this study were male; mean ages ranged from 50.9 years in the 400 mg arhalofenate group to 54.5 years in the placebo group. The mean (±SD) time since the initial gout diagnosis was 7.1 years [±6.7] in Placebo groups and 12.0 years [±8.2] in the 600 mg arhalofenate group. The mean (±SD) number of gout flares in the preceding 3 months were 2.5 (±2.2), 1.4 (±1.2), and 2.1 (±2.4) for the placebo, 400 mg arhalofenate, and 600 mg arhalofenate groups, respectively. The mean (±SD) sUA values at baseline (Day 1) were 9.7 mg/dL (±1.6) in the placebo group, 9.4 mg/dL (±1.1) in the 400 mg arhalofenate group and 9.8 mg/dL (±1.3) in the 600 mg arhalofenate group. A total of 67 (72.0%) patients were randomized to receive double-blind treatment: 23 patients received Placebo, 21 arhalofenate 400 mg, and 23 arhalofenate 600 mg. A total of 64 patients completed the study: 22 patients in Placebo group, 20 patients in arhalofenate 400 mg group, and 22 patients in arhalofenate 600 mg group. After 4 weeks of daily treatment with double-blind study medication, the mean sUA percent (and absolute) changes from baseline (Day 1) in the PP population were: 4.1% (0.2 mg/dL) in the placebo group, −15.4% (1.4 mg/dL) in the 400 mg arhalofenate group and −23% (−2.3 mg/dL) in the 600 mg arhalofenate group. When compared with placebo, the sUA reduction in both of the arhalofenate treatment groups was statistically significant (p<0.0001). A total of 10 patients reported flare during the Treatment Phase: 5 patients (21.7%) in the placebo group, 4 patients (19.0%) in the 400 mg arhalofenate group, and 1 patient (4.3%) in the 600 mg arhalofenate group [FIG. 4]. Of these, 3 patients (13.0%) in the placebo group, 1 patient (4.8%) in the 400 mg arhalofenate group, and 1 patient (4.3%) in the 600 mg arhalofenate group required medication (additional colchicine and/or NSAIDs) [FIG. 4]. The mean duration of Total flares was longer in the placebo group (5.2 days) than in either the 400 mg arhalofenate group (1.3 days) or the 600 mg arhalofenate group (1.0 days) [FIG. 5]. The mean (±SD) duration of Flares Requiring Treatment was also longer in the placebo group (4.7 days) than in either the 400 mg arhalofenate group (2.0) or the 600 mg arhalofenate group (1.0 day) [FIG. 5]. No severe gout flare was reported during the double-blind period. Flares were less severe in the arhalofenate 600 mg group compared to other groups (3 of 5 flares in placebo group, 2 of 4 flares in 400 mg arhalofenate group and 0 of 2 flares in 600 mg arhalofenate group were considered moderate in severity by the investigator).

Example 4

Clinical Trial Evaluating the Effectiveness of Arhalofenate in Combination with Febuxostat Compared to Febuxostat Alone in Serum Uric Acid Reduction and Flare Prevention in Gout Patients with Hyperuricemia Study Design: This was an open-label study to determine the sUA reduction and flare prevention with arhalofenate in combination with febuxostat and compared that with febuxostat alone in gout patients (per criteria of the American Rheumatism Association) with hyperuricemia when arhalofenate administered at 400 mg once daily orally for 2 weeks (Weeks 2-3) and then increased to 600 mg once daily orally for an additional 2 weeks (Weeks 4-5) in addition to 80 mg febuxostat once daily orally (Weeks 1-5). Patients with a recent history of an acute gout flare must have been symptom free for at least 1 week prior to screening.

All patients who met the screening criteria started a 2-week Run-in/Stabilization Phase at the same time as out-patient basis. During this phase, patients on existing urate lowering therapy were asked to discontinue their current therapy for the duration of the study. At the same time, patients also started colchicine 0.6 mg once daily as prophylaxis to prevent potential gout flares. Upon completing the Run-in/Stabilization Phase, patients were reassessed at Day −2 (Visit 2) to confirm the final eligibility for the Treatment Phase. The sUA at this visit must have been ≥8.0 mg/dL and ≤10 mg/dL to qualify for the Treatment Phase. In addition, all safety lab values must have met the eligibility criteria at this visit. Patients successfully meeting the eligibility criteria entered the study site for an in-clinic stay for a total of 37 consecutive days.

The Treatment Phase began on Day 1 and continued for 5 weeks until Day 35. The Treatment Phase consisted of 3 sequential drug dosing periods:

80 mg febuxostat orally once daily from Days 1 through 7 (Febuxostat Period).

80 mg febuxostat plus 400 mg arhalofenate orally once daily from Days 8 through 21 (Febuxostat plus 400 mg arhalofenate Period).

80 mg febuxostat plus 600 mg arhalofenate orally once daily from Days 22 through 35 (Febuxostat plus 600 mg arhalofenate Period).

In addition, all patients continued to receive 0.6 mg colchicine daily for gout flare prophylaxis.

Criteria for Evaluation:

Efficacy of febuxostat plus arhalofenate combination treatment was assessed by the proportion of patients achieving a sUA<6 mg/dL, <5 mg/dL, <4 mg/dL, and <3 mg/dL at Day 22 and Day 36. In addition, absolute and percent changes in sUA at Day 22 and Day 36 from baseline (Day 1) were also evaluated. Gout flares were captured as special interest event in this study. The incidence of gout flares, severity (as assessed either mild, moderate, or severe by the Principal Investigator), and duration (days) were compared between treatment periods.

Results:

A total of 12 patients met the final eligibility criteria at Visit 2 (Day −2) and entered into the in-patient Treatment Phase of the study as a single cohort. On Day 1, after receiving the first dose of febuxostat, 1 patient withdrew consent to continue study participation for personal reason (got a permanent job); the remaining 11 patients completed the study including Follow-up phase. The mean (±SD) time since the initial gout diagnosis was 12.6 years (±7.2). The mean (±SD) number of gout flares in the preceding 3 months was 0.9 (±1.2). The mean (±SD) sUA at baseline was 9.0 mg/dL (±0.8). At Day 8, after one week of daily treatment with 80 mg febuxostat, 11 patients (100%) reached sUA target of <6 mg/dL, 6 patients (55%) reached <5 mg/dL, and 1 patient (9%) reached <4 mg/dL. At Day 22, after 2 weeks of daily treatment with 80 mg febuxostat plus 400 mg arhalofenate (preceded by 80 mg febuxostat daily for 1 week), statistically significantly higher proportion of patients achieved sUA target of <5 mg/dL compared with Day 8 (sUA<5.0 mg/dL in 10 patients, p=0.0455). By Day 36, after 2 weeks of daily treatment with 80 mg febuxostat plus 600 mg arhalofenate (preceded by 80 mg febuxostat daily for 1 week and 80 mg febuxostat plus 400 mg arhalofenate for 2 weeks), statistically significantly higher proportion of patients achieved sUA targets of <5 mg/dL and <4 mg/dL compared with Day 8 (sUA<5.0 mg/dL in 11 patients, p=0.0253; sUA<4.0 mg/dL in 7 patients, p=0.0143).

In this study, gout flare was considered as a special interest event. All patients were taking 0.6 mg colchicine daily as flare prophylaxis for the entire duration of the study. Overall, 4 patients experienced gout flares during the study—2 patients during 1 week of febuxostat only period, 2 patients during 2 weeks of 400 mg arhalofenate plus febuxostat period. No patient reported flare during 2 weeks of 600 mg arhalofenate plus febuxostat period. When adjusted by duration of treatment, 18.2% patients/week during febuxostat only period, and 9.1% patients/week during 400 mg arhalofenate plus febuxostat period reported flare [FIG. 6]. Mean duration of the gout flares during the Treatment Phase was 6.5 days for the febuxostat only period and 4.0 days for the 400 mg arhalofenate plus febuxostat period [FIG. 7]. All of the flares were mild or moderate in severity.

Example 5

Clinical Trial to Evaluate the Role of Arhalofenate Monotherapy (600 mg and 800 mg) in Preventing Gout Flare and Reducing sUA in Gout Patients when Used as a Urate Lowering Agent and Compare that with Allopurinol 300 mg Study Design: This is a multi-center, randomized, double-blind, active and placebo-controlled, parallel group study in gout patients with sUA of ≥7.5 mg/dL and ≤12 mg/dL who experienced at least 3 flares during the past 12 months. Approximately 225 eligible patients will be randomized in a 2:2:2:2:1 ratio into one of the following five treatment groups:
1) Arhalofenate (600 mg) once daily.
2) Arhalofenate (800 mg) once daily.
3) Allopurinol (300 mg) plus colchicine (0.6 mg) once daily.
4) Allopurinol (300 mg) once daily.
5) Placebo once daily.

Study Objectives:
Primary:
To evaluate the efficacy of each of two dose levels of arhalofenate dosed once daily for the prevention of flares in adult gout patients with hyperuricemia.

Secondary:
To evaluate the efficacy of each of two dose levels of arhalofenate in reducing serum uric acid (sUA).

To evaluate whether arhalofenate can effectively reduce acute gout flares without colchicine prophylaxis.

To evaluate the safety and tolerability of each of two dose levels of arhalofenate in this study population.

To select an appropriate dose level of arhalofenate dosed once daily for future trials To measure steady-state arhalofenate concentrations at each of two dose levels of arhalofenate dosed once daily.

To evaluate changes in metabolic parameters of interest in selected patients.

Study Endpoints:
Primary
The incidence of gout flares (mean number of flares per patient) from baseline through Week 12.

In this study, a gout flare is defined as a patient-reported acute articular or bursal pain at rest (exceeding 3.0 cm on a 10.0 cm VAS) typical of a gout attack and deemed (by patient and/or investigator) to require treatment with an anti-inflammatory therapeutic agent, and the presence of at least 2 of the following 3 signs or symptoms: joint swelling, warmth, and tenderness; and at least one of the following: rapid onset of pain, decreased range of motion, redness, or other symptoms similar to a prior gout flare.

Secondary
Key Secondary Endpoints:
Percent sUA reduction from baseline in arhalofenate 800 mg group compared to Placebo group.

Percent sUA reduction from baseline in arhalofenate 600 mg group compared to Placebo group.

Proportion of patients with sUA<6 mg/dL at Week 12 in arhalofenate 800 mg group compared to Placebo group.

The incidence of gout flares from baseline through Week 12 in arhalofenate 600 mg group compared to allopurinol 300 mg group.

Proportion of patients with sUA<6 mg/dL at Week 12 in arhalofenate 600 mg group compared to Placebo group.

Proportion of patients experiencing at least one flare from baseline through week 12.

Proportion of patients experiencing multiple flares from baseline through week 12.

Time from baseline to first flare.

The incidence of flares from baseline through Week 4, Week 5 through Week 8 and Week 9 through Week 12.

Flare composite score (summation of the daily maximum pain severity on VAS during the duration of the flare).

Evaluation of activity limitation during flare via HAQ-II.

Changes from baseline through week 12 in HbA1c and fasting TG in patients with HbA1c>7.0% and TG>150 mg/dL at baseline, respectively.

Adverse events, and changes in vital signs and safety laboratory tests.

Safety-related study drug discontinuations.

Flare-related study drug discontinuations.

Flares that occur during the study will be managed with oral NSAIDs (as $1^{st}$ line therapy) or oral steroids (as $2^{nd}$ line therapy) if the patient cannot tolerate or has an inadequate response to NSAIDs. The patient will be allowed to take other analgesics, according to investigator judgment (e.g. acetaminophen with codeine), as $3^{rd}$ line therapy if the patient cannot tolerate or has an inadequate response to NSAIDs and oral steroids. Colchicine will be prohibited as treatment for flares during the randomized treatment phase.

All patients will be instructed to maintain their current diet and lifestyle, including drinking habits (alcoholic and sugary beverages), throughout the entire study. Patients will be asked to defer initiating any weight loss diets or meaningfully changing their activity level and lifestyle, as such a change may influence sUA levels and potentially trigger a flare, thus confounding a trial of this nature.

Once randomized (entered) into the study, patients will return to the clinic within 7 days to receive study drug supplies and begin dosing (Day 1). Subsequent study visits will occur at the end of week 2, week 4, week 8, and week 12 of dosing.

The patient will be required to report a flare via an electronic device as soon as conveniently possible and preferably before taking pain medication. Flare-related data, such as date and time of onset, pain severity (VAS), and medication taken will be reported by the patient. Once flare data has been entered by the patient, the device will send an alert to the investigator or his/her designee to contact the patient in order to facilitate additional therapy or data entry, as needed.

Sample Size:
This study is powered to detect a treatment group difference in flare rate (flares per patient) of 50% versus the control group (group 4, allopurinol 300 mg). Power calculations (using methodology for comparisons of incidence rates) indicate that a sample size of 50 patients per treatment group should provide 80% power, based on the use of a two-sided, two-sample test at the 5% level of significance, to detect a 50% treatment group difference, which is a conservative estimate of the expected treatment effect.

In this study, the placebo control group will be used for sUA comparisons (percent reduction and proportion of patients achieving sUA<6 mg/dL) only. Power calculations indicate that a sample size of 25 patients in this arm should provide 80% power, based on the use of a two-sided, two-sample test at the 5% level of significance, to detect a 50% treatment group difference.

Efficacy Analyses:
For the efficacy endpoint of flare rate (mean flare per patient from Day 1 through week 12), the primary analysis will compare the arhalofenate 800 mg group to the allopurinol 300 mg group using a two-sided test at the 5% level of significance.

The following key secondary analyses will be conducted using a hierarchical procedure (Westfall and Krishen 2001) to control the overall level of significance, in the order shown below:

Arhalofenate 800 mg group vs Placebo for percent sUA reduction.

Arhalofenate 600 mg group vs Placebo for percent sUA reduction.

Arhalofenate 800 mg group vs Placebo for proportion of patients with sUA<6 mg/dL.

Arhalofenate 600 mg group vs Allopurinol 300 mg for flare rate.

Arhalofenate 600 mg group vs Placebo for proportion of patients with sUA<6 mg/dL.

The above hypotheses will be tested using two-sided tests at the 5% level of significance, but a specified comparison will only be tested if the primary efficacy analysis and all previously conducted key analyses are statistically significant (p<0.05).

While the foregoing description describes specific embodiments, those with ordinary skill in the art will appreciate that various modifications and alternatives can be developed. Accordingly, the particular embodiments and examples described above are meant to be illustrative only, and not to limit the scope of the invention, which is to be given the full breadth of the appended claims, and any and all equivalents thereof.

What is claimed is:

1. A method for decreasing the number, duration, frequency, or intensity of gout flares, experienced by a subject during initiation or maintenance of therapy for uric acid lowering, comprising administration to the subject of a therapeutically effective amount of a flare decreasing agent that is selected from the group consisting of (−)-halofenate and (−)-halofenic acid, or a pharmaceutically acceptable salt thereof, and substantially free from its (+)-enantiomer.

2. The method of claim 1 where the flare decreasing agent is (−)-halofenate.

3. The method of claim 1 where the flare decreasing agent is (−)-halofenic acid or a pharmaceutically acceptable salt thereof.

4. The method of claim 1 where the therapeutically effective amount of the flare decreasing agent is between about 50 mg/day and about 1000 mg/day.

5. The method of claim 4 where the therapeutically effective amount of the flare decreasing agent is between about 400 mg/day and about 1000 mg/day.

6. The method of claim 5 where the therapeutically effective amount of the flare decreasing agent is 400, 600, or 800 mg/day.

7. The method of claim 1 further comprising concomitant administration to the subject of a therapeutically effective amount of a flare prophylaxis agent or a pain management agent.

8. The method of claim 7, where the concomitant administration comprises concurrent administration of the flare decreasing agent and the flare prophylaxis agent or pain management agent.

9. The method of claim 7 where the concomitant administration comprises sequential administration of the flare decreasing agent and the flare prophylaxis agent or pain management agent.

10. The method of claim 7 where the flare decreasing agent is (−)-halofenate.

11. The method of claim 7 where the flare decreasing agent is (−)-halofenic acid or a pharmaceutically acceptable salt thereof.

12. The method of claim 7 where the therapeutically effective amount of the flare decreasing agent is between about 50 mg/day and about 1000 mg/day.

13. The method of claim 12 where the therapeutically effective amount of the flare decreasing agent is between about 400 mg/day and about 1000 mg/day.

14. The method of claim 13 where the therapeutically effective amount of the flare decreasing agent is 400, 600, or 800 mg/day.

15. The method of claim 7 where the flare prophylaxis agent or pain management agent is an NSAID, an opiate, or colchicine.

16. The method of claim 15 where the flare prophylaxis agent or pain management agent is colchicine.

* * * * *